United States Patent
Mann et al.

(10) Patent No.: US 6,605,094 B1
(45) Date of Patent: Aug. 12, 2003

(54) INTEGRATED SUBCUTANEOUS TUNNELING AND CARRYING TOOL

(75) Inventors: Carla M. Mann, Los Angeles, CA (US); Kenny K. Chinn, Rosemead, CA (US)

(73) Assignee: Advanced Bionics Corporation, Sylmar, CA (US)

( * ) Notice: Subject to any disclaimer, the term of this patent is extended or adjusted under 35 U.S.C. 154(b) by 106 days.

(21) Appl. No.: 09/702,422

(22) Filed: Oct. 31, 2000

Related U.S. Application Data

(60) Provisional application No. 60/166,560, filed on Nov. 19, 1999.

(51) Int. Cl.[7] ............................................. A61B 19/00
(52) U.S. Cl. .................................................... 606/129
(58) Field of Search ...................... 606/129, 1; 601/36, 601/119, 131

(56) References Cited

U.S. PATENT DOCUMENTS

| | | | |
|---|---|---|---|
| 5,163,912 A | 11/1992 | Gay et al. ................... 607/164 |
| 5,275,611 A | 1/1994 | Behl ........................... 606/198 |
| 5,417,208 A | 5/1995 | Winkler ....................... 128/642 |
| 5,667,514 A | 9/1997 | Heller ......................... 606/108 |
| 5,722,425 A | 3/1998 | Bostrom ...................... 128/772 |
| 5,728,148 A | 3/1998 | Bostrom et al. ............. 607/116 |
| 5,752,937 A | 5/1998 | Otten et al. ................. 604/161 |
| 5,782,841 A | 7/1998 | Ritz et al. .................... 606/129 |
| 6,004,326 A | 12/1999 | Castro et al. ................. 606/99 |
| 6,304,785 B1 * | 10/2001 | McCreery et al. .......... 606/129 |
| 6,324,414 B1 * | 11/2001 | Gibbons et al. ............. 606/129 |

FOREIGN PATENT DOCUMENTS

| WO | 9720530 | 6/1997 |
|---|---|---|
| WO | 0002623 | 1/2000 |

* cited by examiner

*Primary Examiner*—Michael J. Milano
*Assistant Examiner*—Jessica Baxter
(74) *Attorney, Agent, or Firm*—Laura Haburay Bishop; Bryant R. Gold

(57) ABSTRACT

A subcutaneous tunneling and carrying tool has a handle, a rod, and a carrier. The tool is used in connection with the implantation of electrical stimulators within the body, and more particularly facilitates the surgical procedure in the connection of an electrode lead extension to the implantable stimulator when the electrode and stimulator may not be co-located. In one embodiment, tunneling is accomplished by a tip that also serves to connect the tool to a disposable carrier in which the lead extension connector is packaged. In another embodiment the carrier comprises a carrier body and a removable cover, wherein the carrier cover covers a carrier cavity during tunneling and includes a tunneling end, and the carrier cover is removed after tunneling to expose the carrier cavity, into which carrier cavity the electrode lead extension is inserted to carry back through the tunnel.

18 Claims, 11 Drawing Sheets

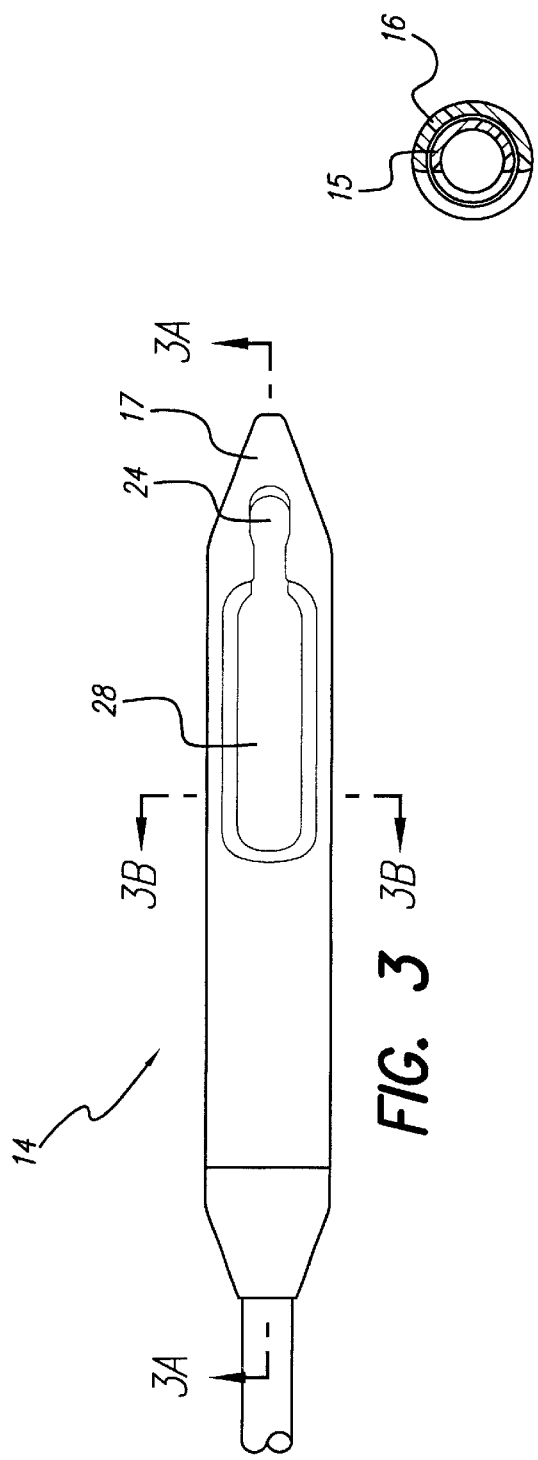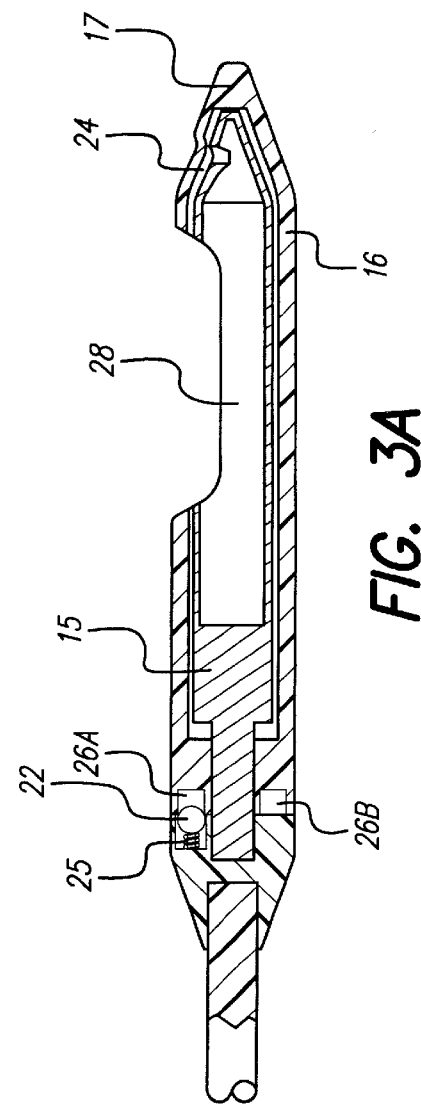

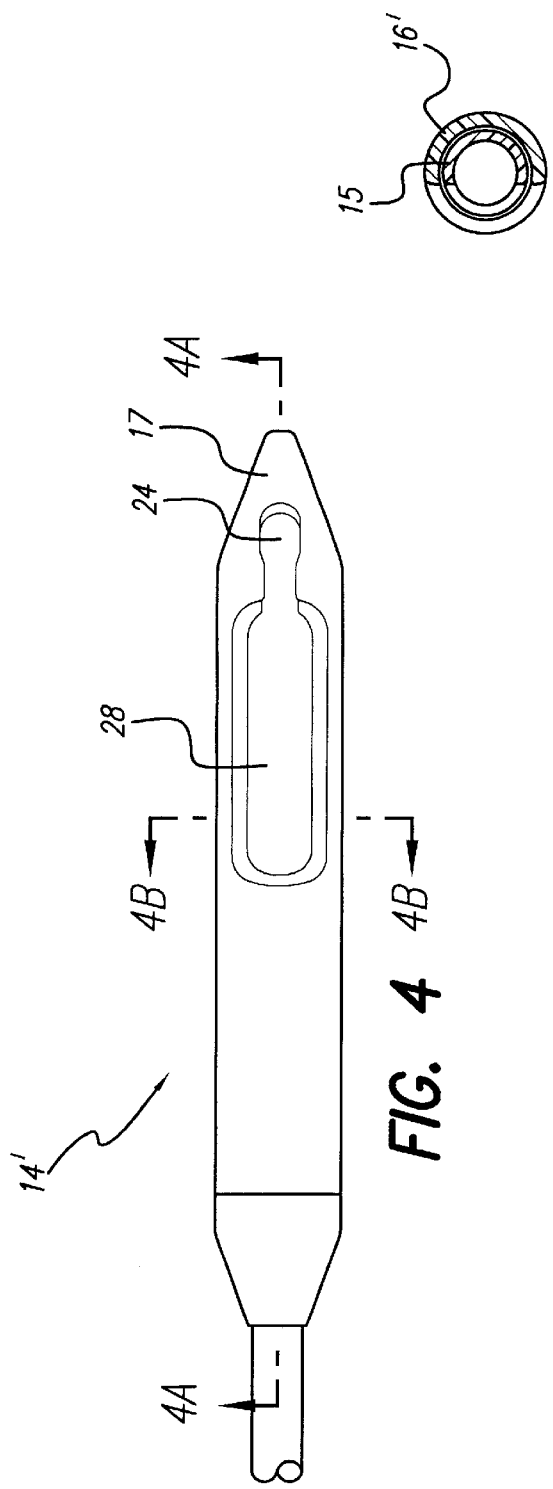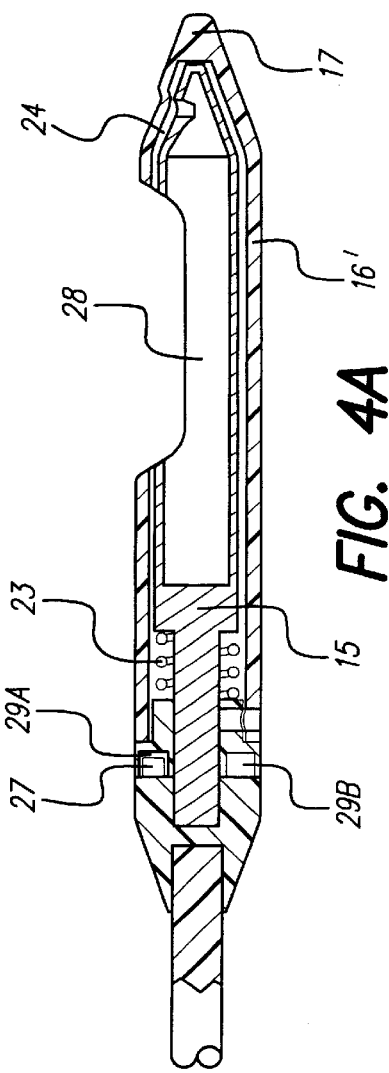

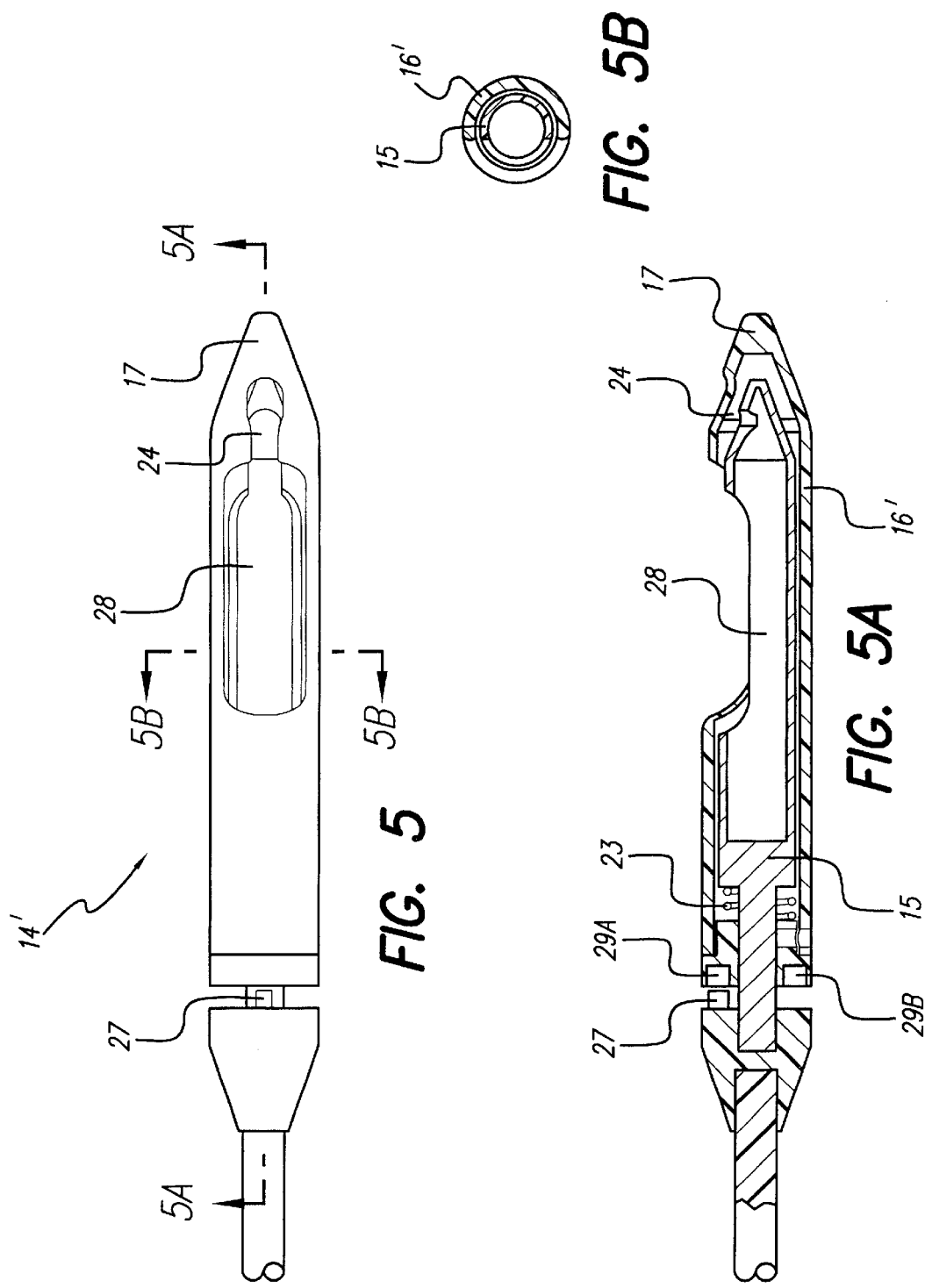

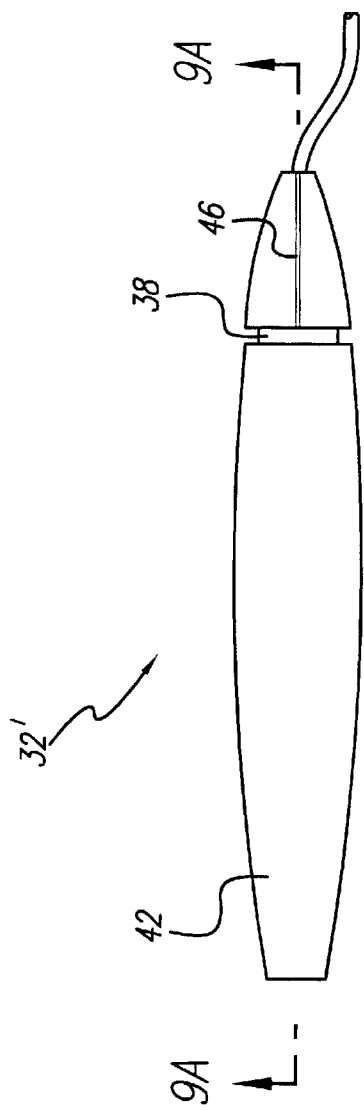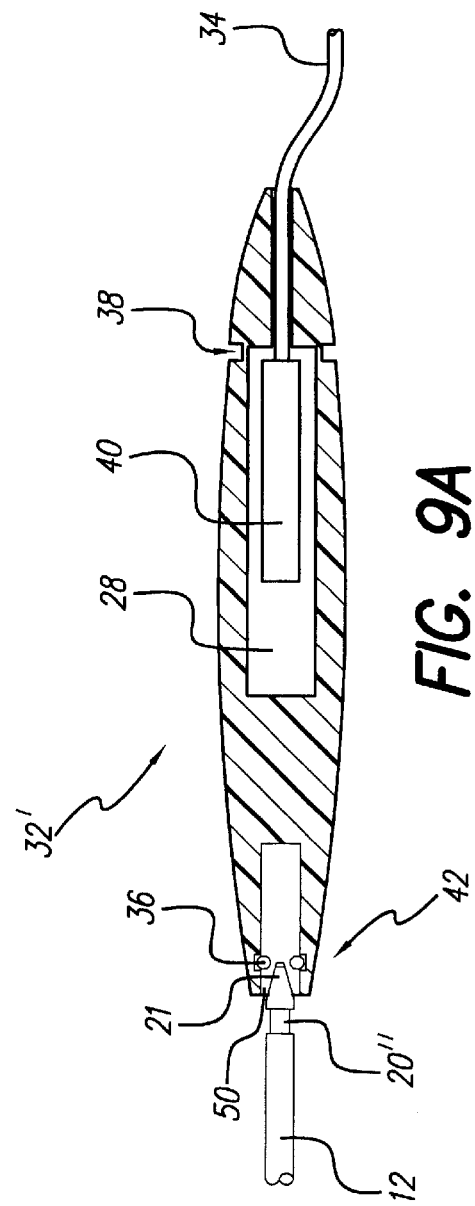

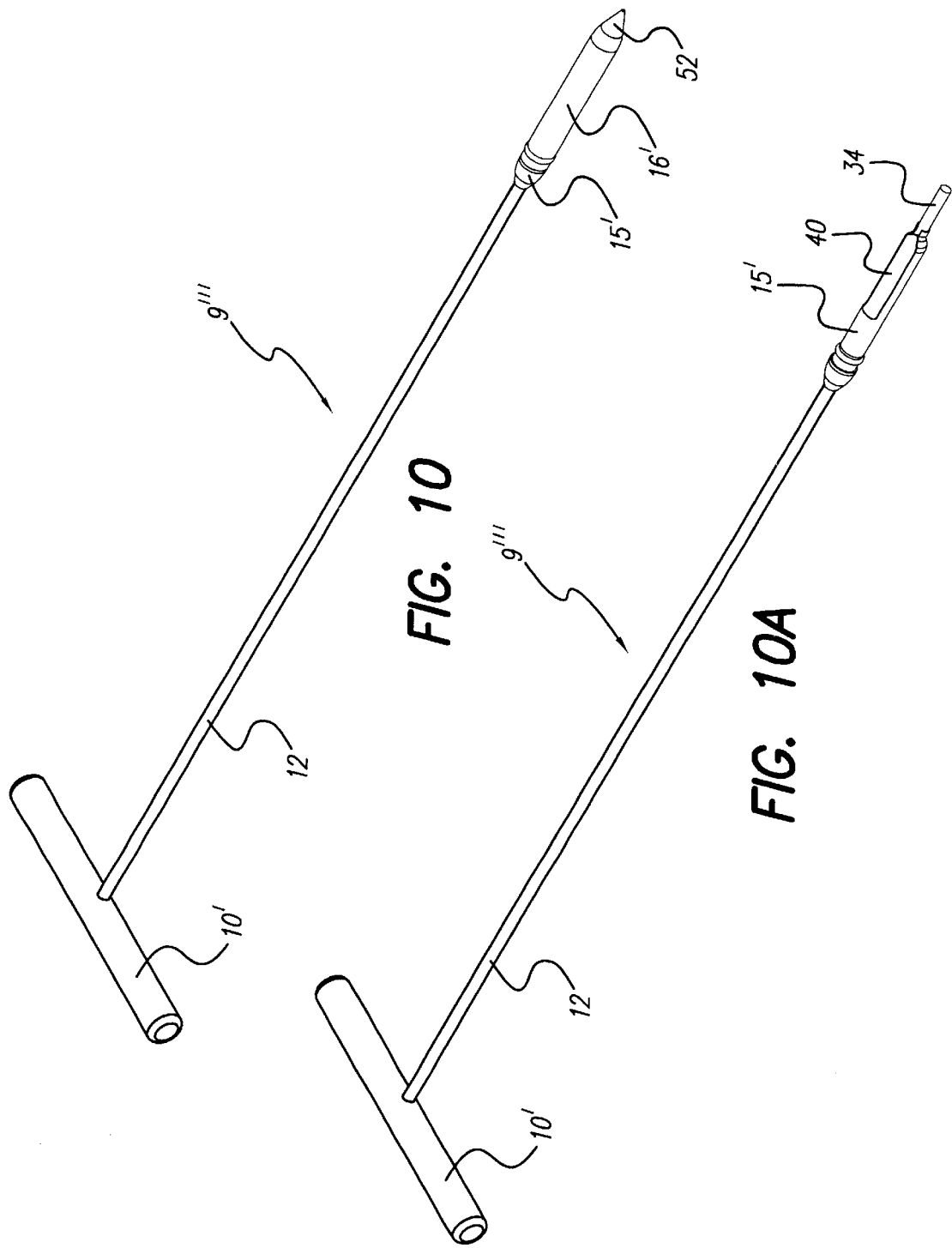

INTEGRATED SUBCUTANEOUS TUNNELING AND CARRYING TOOL

The present application claims the benefit of U.S. Provisional Application Serial No. 60/166,560, filed Nov. 19, 1999 which application is incorporated herein by reference.

BACKGROUND OF THE INVENTION

The present invention relates to implantable medical devices and more particularly to a tool for use in surgically implanting such devices. A common role for such an implantable device is nerve or muscle stimulation and more particularly Spinal Cord Stimulation (SCS). SCS systems typically include an implantable pulse generator (IPG) which is a source of stimulation current, and an implantable electrode array, which provides the stimulation current to the nerves to be stimulated. In many cases where such devices are utilized, the electrode array is remote from the location of the IPG. In such cases, an electrode lead extension is used to connect the IPG to the electrode array. For example, in the case of spinal cord stimulation, the electrodes providing the stimulation current to the nerves must be positioned adjacent to the spinal cord, but sufficient space is not available for the IPG in the area adjacent to the electrodes. In this example, the IPG must be located remotely from the electrode array and a tunneling tool is required to first create a subcutaneous tunnel from the location of the electrode lead to the location of the IPG, and then to carry the electrode lead extension back through the tunnel to the electrode lead.

Existing subcutaneous tunneling and carrying tools require a separate tunneling tip and carrying tip. After the tunnel is created using the tunneling tip, the tunneling tip must be removed and the carrying tip attached. The common method of attachment is a threaded adapter on the end of a shaft. This approach requires that the tunneling tip be removed by unscrewing and the carrying tip be attached similarly. The requirement to unscrew one tip and screw on another tip adds to the complexity of the surgical procedure. If the threads are damaged in the process of installing the carrier, a new tunneling tool and/or carrier must be used. The need to keep surgical procedures as simple and error free as possible dictates that a more robust approach be found.

SUMMARY OF THE INVENTION

The present invention advantageously addresses the above and other needs by providing an integrated subcutaneous tunneling and carrying tool, functionally similar to existing tools, that eliminates the need to unscrew a tunneling tip and screw on a separate carrying tip. The tool provided by the present invention is used to create a tunnel through body tissue, and then to carry an electrode lead extension through the tunnel for connection to the electrode lead, without requiring the manipulation of threaded tips. The electrode lead extension includes a female lead extension connector which connects with a male connector on the end of the electrode lead. A tool according to the present invention includes either a cavity that the lead extension connector is inserted into, a male connector similar to the connector on the electrode lead, which male connector is connected to the lead extension connector, or a second male connector, which second connector connects to a disposable carrier which the lead extension connector is carried in. At least four embodiments of the present invention are envisioned.

In a first embodiment of the integrated subcutaneous tunneling and carrying tool, a carrier is employed that serves both the function of tunneling and carrying. After the tool has completed the tunneling process, a cover that is part of the carrier is opened by a simple pull and twist action, and the lead extension connector is inserted into the carrier. Then, the tool is pulled back through the tunnel, carrying the lead extension connector and attached electrode lead extension.

In a second embodiment, the integrated subcutaneous tunneling and carrying tool includes a mating connector designed to connect with the lead extension connector and attached electrode lead extension. The mating connector is the same basic shape as the corresponding male connector on the electrode lead to which the lead extension connector attaches, and also has a tip suitable for tunneling. After creating the tunnel and connecting the lead extension connector, the tool is pulled back through the tunnel, pulling the electrode lead extension with it. In this embodiment, the section of the tool adjacent to the mating connector may be enlarged to provide additional clearance for pulling the lead extension connector and electrode lead extension through the tunnel.

In a third embodiment, the lead extension connector of the electrode lead extension is delivered packaged in a disposable carrier. The disposable carrier includes a receptacle with an attaching mechanism. The integrated subcutaneous tunneling and carrying tool includes a mating connector designed to both tunnel and to engage the attaching mechanism of the disposable carrier. After the tunneling tool is pushed through the tissue, the disposable carrier is attached to the mating connector and then pulled back through the tunnel. After the carrier is pulled through the tunnel, the lead extension connector is removed, And the disposable carrier is discarded.

In a fourth embodiment, the tool includes a carrier permanently attached to the tool. The carrier comprises a carrier body and a carrier cover, which carrier cover has a pointed end for tunneling. After the tunnel has been made, the cover is removed and discarded. The lead extension connector is inserted into a cavity in the carrier body, and the electrode lead extension is pulled back through the tunnel.

It is thus a feature of the present invention to provide several embodiments embodiments of a simple-to-use tool, which provides a tunneling capability, and a carrying capability, without difficult manipulation of tool components.

BRIEF DESCRIPTION OF THE DRAWINGS

The present invention will be described in conjunction with the following drawings wherein:

FIG. 3 shows details of the first embodiment of a carrier of the first embodiment of the tool with the carrier cover in the open position;

FIG. 3A shows a cross section of the carrier shown in FIG. 3 taken along the lines 3A—3A of FIG. 3 and illustrates the cover locking feature;

FIG. 3B shows a second cross section of the carrier shown in FIG. 3 taken along the lines 3B—3B of FIG. 3;

FIG. 4 depicts the details of a second embodiment of the carrier element of the first tool embodiment;

FIG. 4A shows a cross section of the carrier shown in FIG. 4 taken along the lines 4A—4A of FIG. 4 and illustrates a second method for providing a cover lock;

FIG. 4B shows a second cross section of the carrier shown in FIG. 4 taken along the lines 4B—4B of FIG. 4;

FIG. 5 depicts the details of the second embodiment of the carrier element of the first tool embodiment with the carrier cover pulled forward to allow the cover to be rotated between the open and the closed positions;

FIG. 5A shows a cross section of the carrier shown in FIG. 5 taken along the lines 5A—5A of FIG. 5 and further illustrates the second method for providing a cover lock wherein the cover lock is disengaged;

FIG. 5B shows a second cross section of the carrier shown in FIG. 5 taken along the lines 5B—5B of FIG. 5;

FIG. 9 depicts a variation of the third embodiment with a break apart carrier;

FIG. 9A shows a cross sectional view of the embodiment in FIG. 9 taken along the lines 9A—9A of FIG. 9 and illustrates a mating connector and cooperating connector port which provide a pivotal connection;

FIG. 10 depicts a fourth embodiment of the tunneling and carrying tool utilizing a removable carrier cover, with the carrier cover in place;

FIG. 10A shows the fourth embodiment of the tool with the carrier cover removed, and an electrode lead connector inserted into a carrier cavity of the carrier.

Corresponding reference characters indicate corresponding components throughout the several views of the drawings.

DETAILED DESCRIPTION OF THE INVENTION

The following description is of four alternative embodiments for carrying out the present invention. These include the best mode presently contemplated. The descriptions are not to be taken in a limiting sense, but are made merely for the purpose of describing the general principles of the invention. The scope of the invention should be determined with reference to the claims.

Figure 1C:
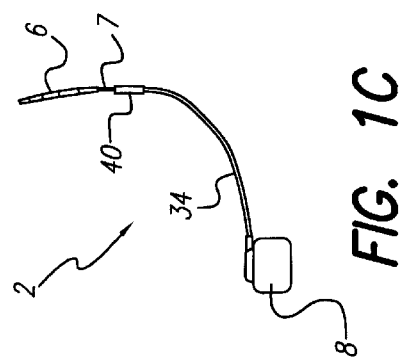
FIG. 1C shows a more detailed view of the SCS system components.
Figure 1B:
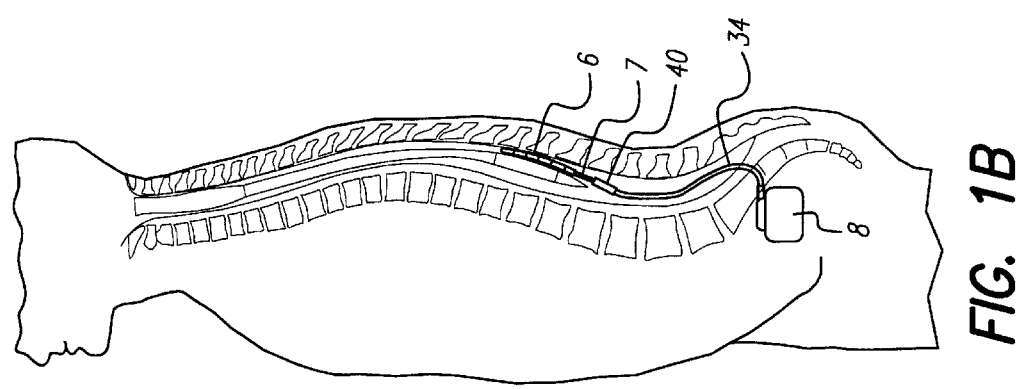
FIG. 1B depicts another typical implant location of an SCS system with the IPG implanted above the buttock.
Figure 1A:
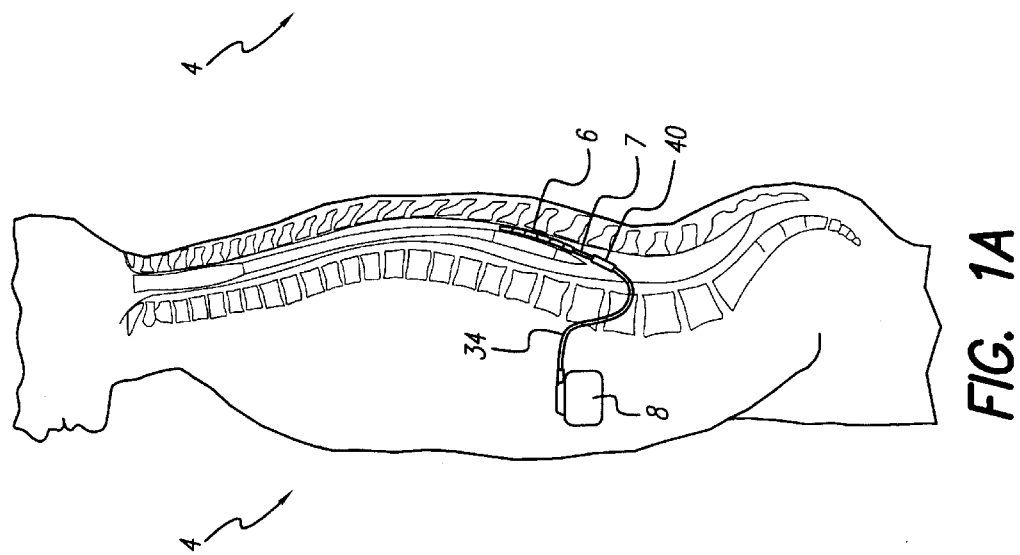
FIG. 1A depicts a typical Spinal Cord Stimulation (SCS) system implant location with an electrode adjacent to the spinal cord, and an implantable pulse generator (IPG) beneath the rib cage.

Typical implants of a Spinal Cord Stimulation (SCS) system in a patient 4 is shown in FIG. 1A and in FIG. 1B. The SCS system is comprised of at least one electrode 6, an electrode lead extension 34, and an implantable pulse generator (IPG) 8. The electrode 6 includes an electrode lead 7, and the electrode lead extension 34 includes a lead extension connector 40. Generally, the electrode 6 and the IPG 8 cannot be co-located due to space limitations. Typical locations for the IPG 8 are beneath the rib cage as shown in FIG. 1A or above the buttock as shown in FIG. 1B. This is because the electrode 6 must be located at the stimulation site, but space is not always available for the IPG 8 at the same location as the stimulation site. In these cases, a tool must be used to first create a subcutaneous tunnel through the body tissue from the site of the electrode lead 7 exit from the spinal column, to the IPG 8. Once the tunnel has been created, the lead extension connector 40 and attached electrode lead extension 34 are carried back through the tunnel and removable attached ( e.g, plugged into) the electrode lead 7.

As seen in FIG. 1C, and as is evident from FIGS. 1A and 1B, the system 2 includes three main components, the electrode 6, the electrode lead extension 34, and the IPG 8. The IPG 8 produces electrical current. The electrode lead extension 34 is connected to the IPG 8, and carries the electrical current to the electrode 6. The electrode 6 delivers the electrical current to the nerve. The electrode lead 7 has an end that is permanently connected to the electrode 6, and has another end with a connector that exits the spinal column. The electrode lead connector 40 removably connects the electrode lead extension 34 to the electrode lead 7 and extends from the electrode lead 7 to the IPG 8.

Figure 2:
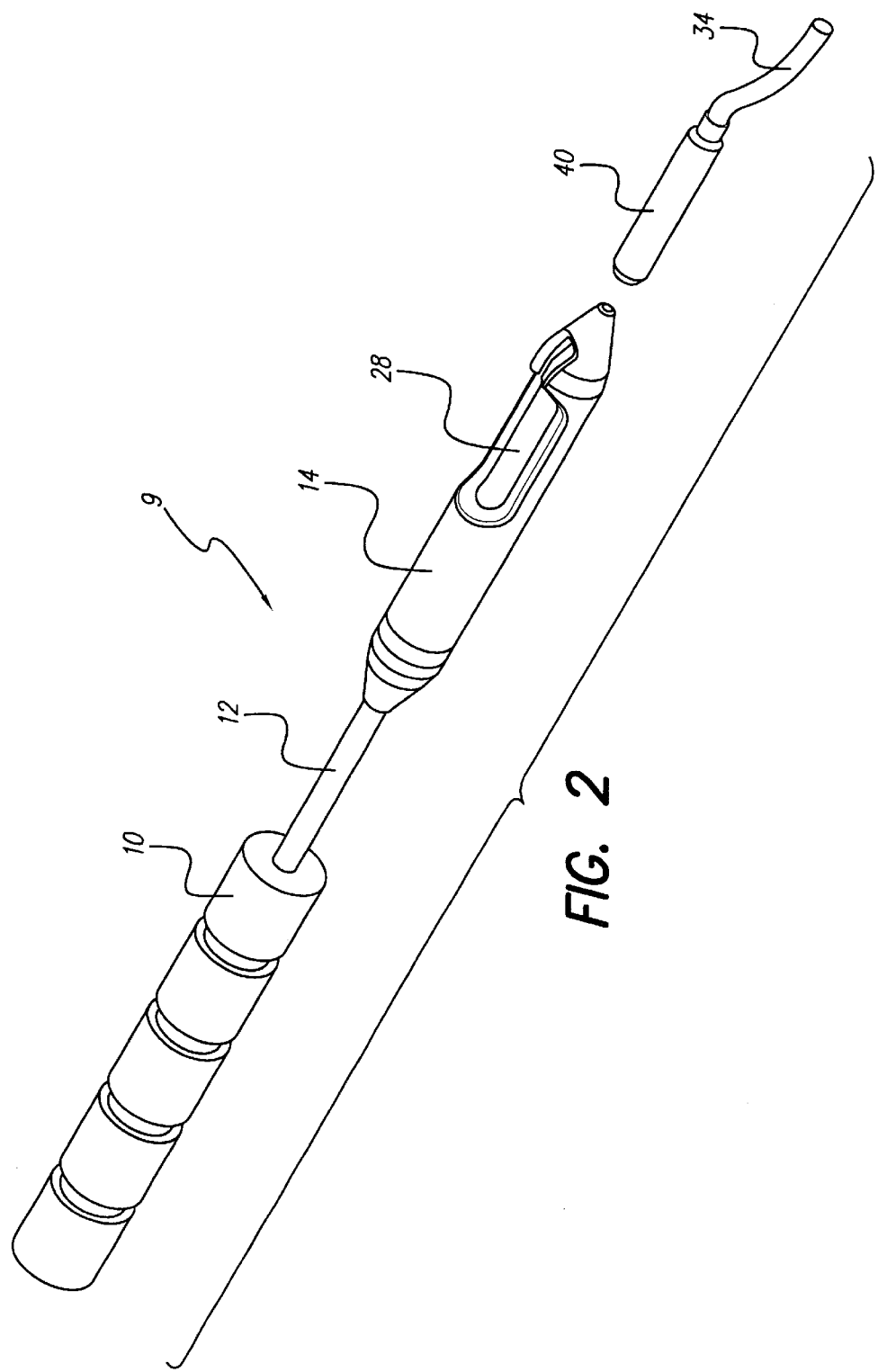
FIG. 2 depicts a first embodiment of the tunneling and carrying tool with the carrier cover in an open position and carrier cavity exposed, and a lead extension connector suitable for carrying in the carrier cavity.

The present invention relates to an integrated subcutaneous tunneling and carrying tool. First the tool is used to create a subcutaneous tunnel from the site where the electrode lead 7 exits from the spinal column, to the implant location of the IPG 8. Then the tool is used to carry the electrode lead extension 34 from the IPG 8 to the electrode lead 7 so that the lead extension connector 40 may be detachably connected to the electrode lead 7. One embodiment of such a tool 9 is shown in FIG. 2 and comprises a handle 10, a rod 12 and a carrier 14. The carrier 14 has a pointed end that is used to create the tunnel from the electrode lead 7 to the IPG 8, and a carrier cavity 28 used to carry the lead extension connector 40 and attached electrode lead extension 34 back through the tunnel. Thus, in this embodiment of the tool, the carrier 14 is used for both tunneling and carrying.

As shown in more detail in FIG. 3, the first embodiment of the carrier 14 of the tool 9 includes a carrier tunneling end 17 for tunneling, the carrier cavity 28 into which the lead extension connector 40 is inserted for carrying through the tunnel, and a lead guide 24 in which a portion of the electrode lead extension 34 is removably pressed to retain the lead extension connector 40 and attached electrode lead extension 34 while they are carried through the tunnel.

FIG. 3A shows a sectional view of the carrier 14 taken along the line 3A—3A of FIG. 3. The carrier cover 16 is shown as surrounding the carrier body 15. The carrier cover 16 is rotatably attached to the carrier 14 and has two locking positions. In the position shown in FIG. 3, the cover is in the open position and is aligned with the carrier cavity 28 allowing the lead extension connector 40 to be removably inserted into the carrier cavity 28. To perform the tunneling process, the carrier cover 16 is rotated 180 degrees into the closed position where it covers the carrier cavity 28 to prevent body tissue from entering the carrier cavity 28, or snagging the carrier cavity 28. The carrier cover 16 also includes the carrier tunneling end 17 shaped to facilitate use of the carrier 14 for tunneling. When the tunneling procedure has been completed, the carrier cover 16 is pulled toward the carrier tunneling end 17 and rotated to expose the carrier cavity 28.

The carrier cover 16 locking mechanism is also shown in the sectional view in FIG. 3A. The locking mechanism comprises a spring 25 pushing a locking ball 22 to cooperating with either of two ball receptacles 26A, 26B in the carrier cover 16 to lock the carrier cover 16 into an open or closed position. When twisting torque is applied to the carrier cover 16, the locking ball 22 pushes against the spring 25, thus permitting the carrier cover to the rotated. When the locking ball 22 is aligned with either ball receptacle 26A, 26B the locking ball 22 is pushed forward by the spring 25 and locks the carrier cover 16.

A second cross section of the second embodiment of the carrier 14 is shown in FIG. 3B taken along the line 3B—3B of FIG. 3. This view further illustrates the relationship of the carrier body 15 and the carrier cover 16.

A second embodiment of the carrier 14' is shown in FIG. 4. The only difference between the first and second embodiments of the carrier 14 is the method of locking the carrier cover 16 into the open or closed positions.

A sectional view of the second carrier 14' is shown in FIG. 4A taken along the line 4A—4A of FIG. 4. The cover spring 23 is shown forcing the second cover 16' to the rear (to the left in FIG. 4A), which is into the locked position. The locking is accomplished by locking pin 27 engaging pin receptacle 29A. The carrier cover 16' is placed into the closed position by pulling the carrier cover 16' to a forward position (to the right in FIG. 4A), rotating the carrier cover 180 degrees relative to the carrier body 15, and allowing the cover spring 23 to push the carrier cover 16' to the rearward position (to the left in FIG. 4A), so that the locking pin 27 engages the second pin receptacle 29B.

A second cross sectional view of the second embodiment of the carrier 14 is shown in FIG. 4B taken along the line 4–4B of FIG. 4. This view serves to further illustrate the relationship of the carrier body 15 and the carrier cover 16'.

A second view of the second carrier 14' is shown in FIG. 5 with the carrier cover pulled forward to reveal the locking pin 27. When the carrier cover 16' is pulled forward as shown, it may be manually rotated into the open or closed position.

A second sectional view of the second locking embodiment is shown in FIG. 5A taken along the line 5A—5A of FIG. 5. Here the locking pin 27 is shown disengaged from the pin receptacle 29A. The cover spring 23 is shown in the compressed condition.

An additional cross section of this embodiment of the carrier 14 is shown in FIG. 5B taken along the line 5B—5B of FIG. 5. This view serves to further illustrate the relationship of the carrier body 15 and the carrier cover 16'.

It will be apparent to those skilled in the art that many equivalent methods of locking the cover in the open or closed position are possible. These include other spring arrangements, spring loaded detents, friction fits, etc., and these other methods are intended to fall within the scope of the present invention.

Figure 6:
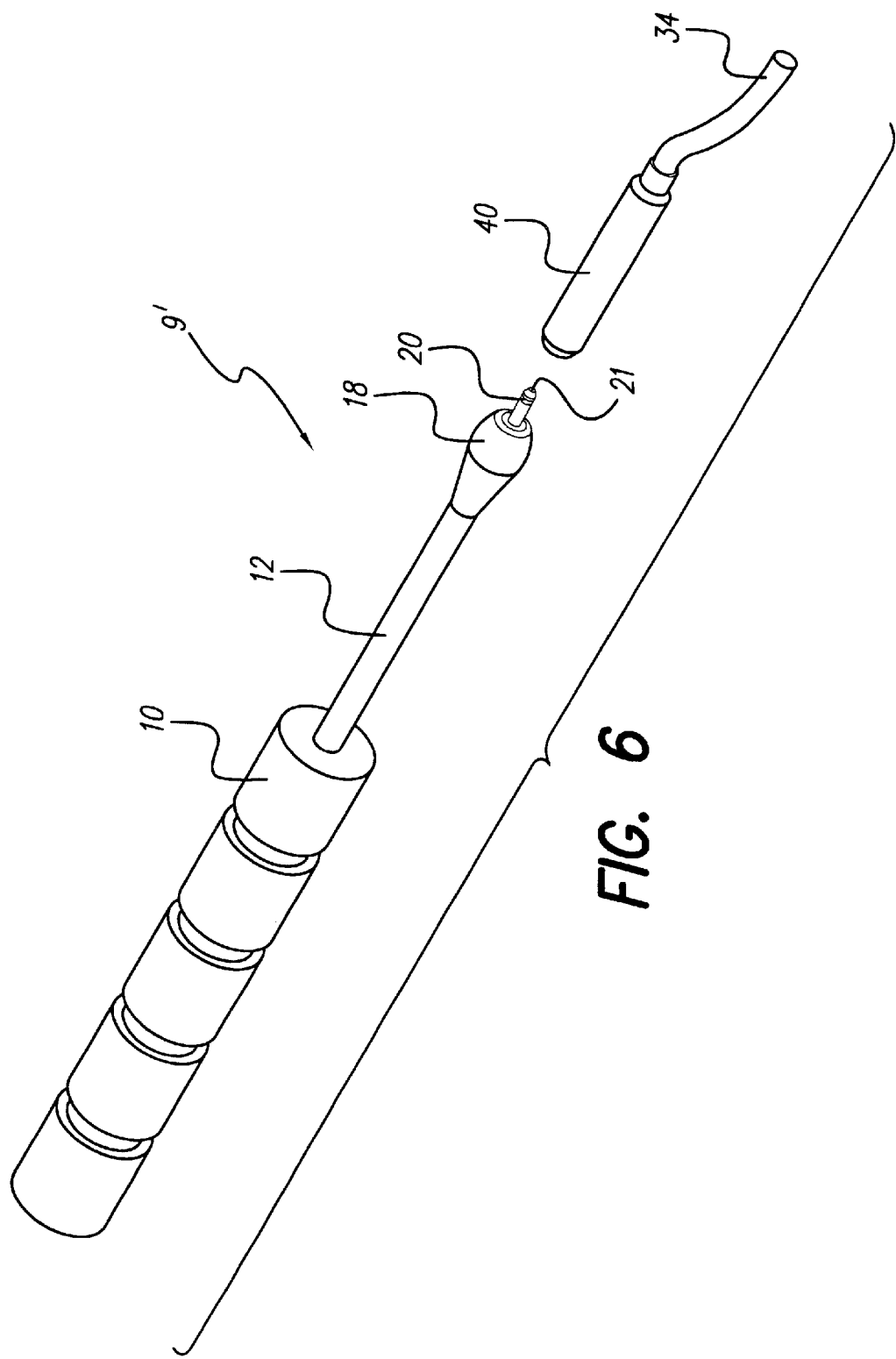
FIG. 6 depicts a second embodiment of the tunneling and carrying tool utilizing a mating connector which engages the lead extension connector and an enlarged section to expand the tunnel for easier passage of the electrode lead extension.

A second embodiment of a tunneling and carrying tool, made in accordance with the present invention, a tool 9', is shown in FIG. 6. The tool 9' includes a tissue expander 18 and mating connector 20. The mating connector 20 includes a tunneling end 21 which is shaped to facilitate the tunneling function. The contour of the mating connector 20 matches the basic shape of a male connector on the end of the electrode lead 7 and is able to engage (plug into) the lead extension connector 40. The tissue expander 18 is located behind the mating connector 20. The purpose of the tissue expander 18 is to expand the tunnel in order to reduce the drag on the lead extension connector 40 and electrode lead extension 34, when the lead extension connector 40 and electrode lead extension 34 are pulled through the tunnel.

Figure 7:
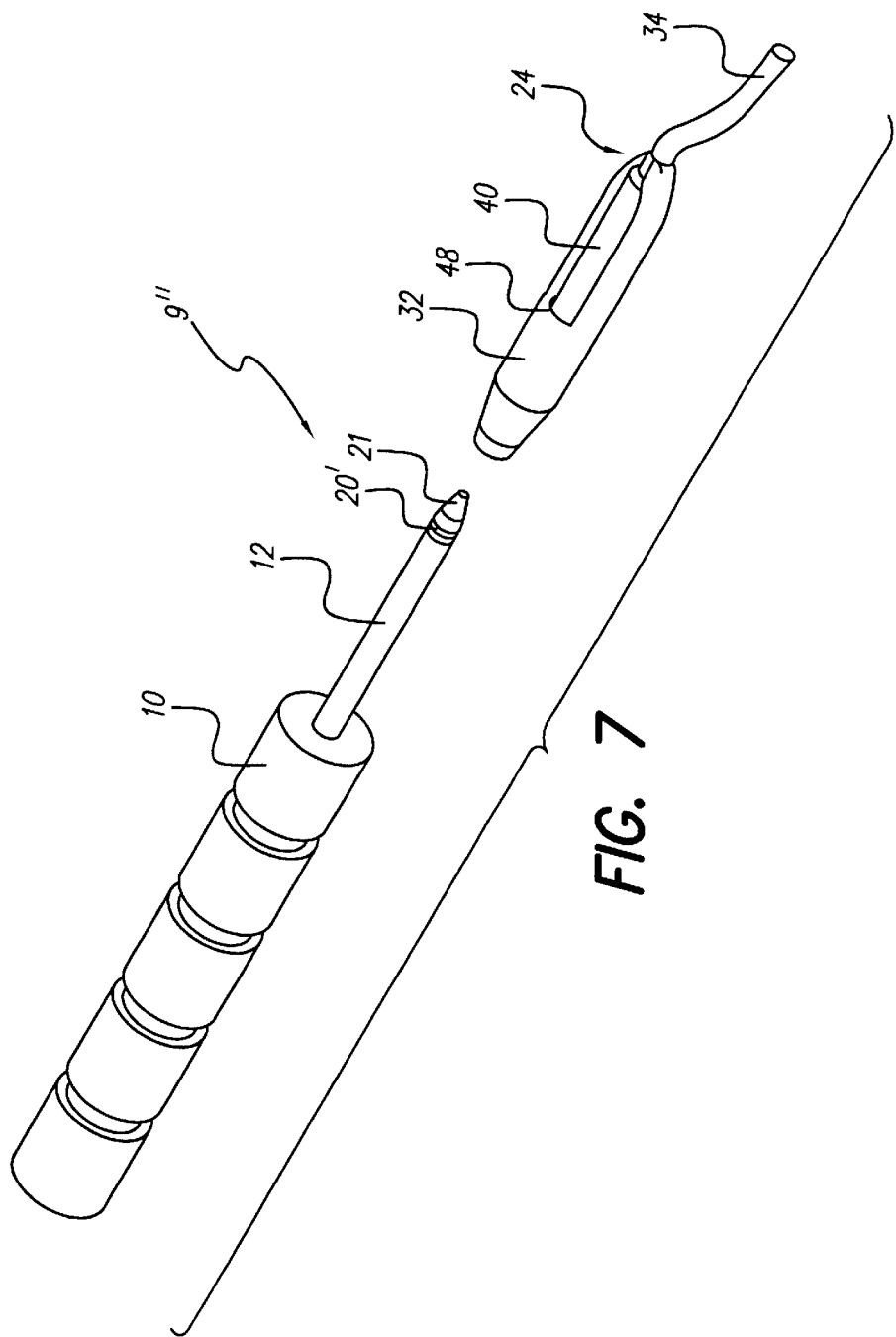
FIG. 7 depicts a third embodiment of the tunneling and carrying tool which includes a second mating connector and a detachable carrier.

A third embodiment of the present invention comprises a tool 9", as shown in FIG. 7. The tool 9" includes a disposable carrier 32. The electrode lead extension 34 is shipped from the manufacturer with the lead extension connector 40 inserted into the disposable carrier 32. The tool 9" further includes a second mating connector 20' which is designed to engage the disposable carrier 32. The mating connector 20' includes the tunneling end 21 as described in FIG. 6.

Figure 8:
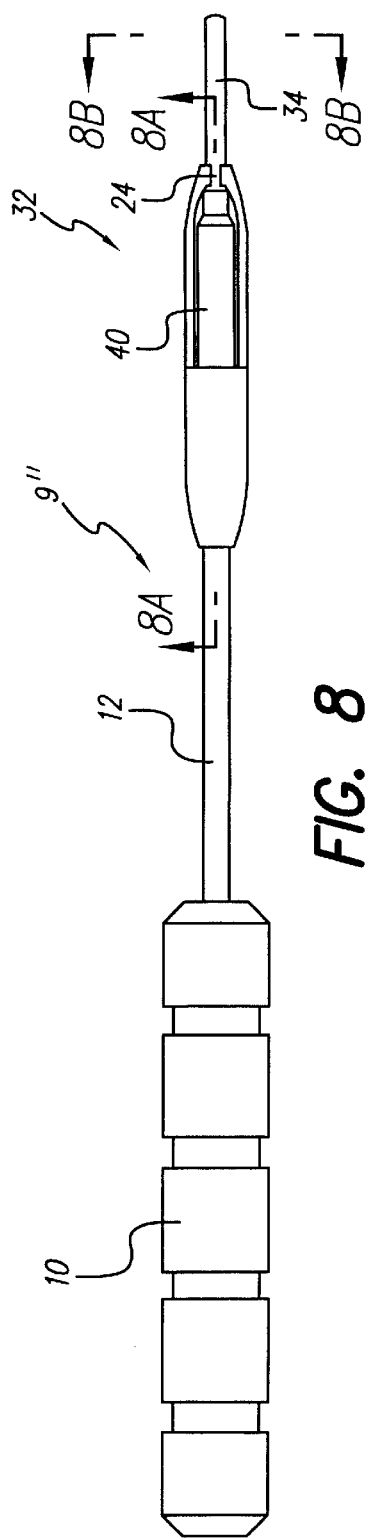
FIG. 8 shows details of the detachable carrier of the third embodiment.

A top view of the tool 9" is illustrates in FIG. 8 and shows the disposable carrier 32 connected to the rod 12 of the tool 9". The lead extension connector 40 is shown resting in the disposable carrier 32, and a section of the electrode lead extension 34 is shown removably inserted into the lead guide 24.

Figure 8B:
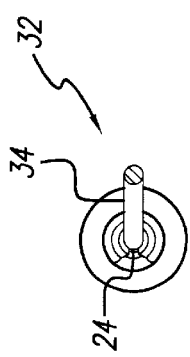
FIG. 8B shows a second cross section of the carrier shown in FIG. 8 taken along the lines 8B—8B of FIG. 8.
Figure 8A:
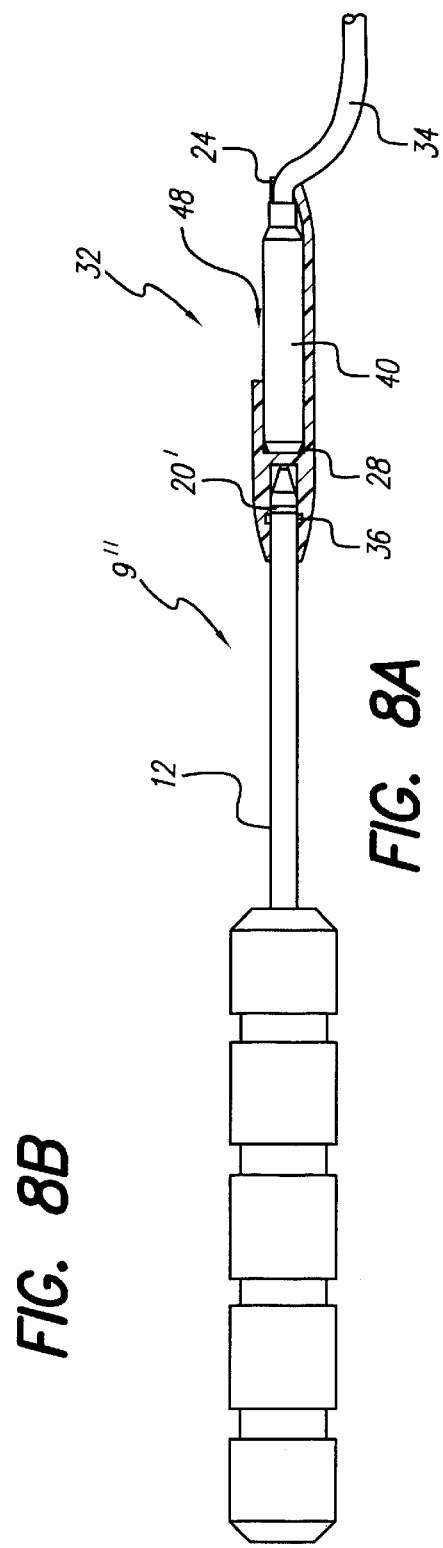
FIG. 8A shows a cross section of the carrier shown in FIG. 8 taken along the lines 8A—8A of FIG. 8.

The sectional view shown in FIG. 8A, taken along the line 8A—8A of FIG. 8, shows a garter spring 36, contained in the disposable carrier 32, that disengagably engages the mating connector 20', to attach the disposable carrier 32 to the rod 12. It will be apparent to those skilled in the art.that many equivalent methods of attaching the disposable carrier to the rod 12 exist and the present invention is not intended to be limited to the embodiment recited herein.

The disposable carrier 32 defines a carrier cavity 28 into which the lead extension connector 40 is removably insertable through a cavity opening 48. The disposable carrier 32 further defines a lead guide 24 into which a section of the electrode lead extension 34 is removably pressed to help retain the lead extension connector 40 in the carrier cavity 28. In a preferred embodiment, the lead extension connector 40 is inserted into the carrier cavity 28 as part of the manufacturing process and is delivered in this configuration. However, the disposable carrier 32 and electrode lead extension 34 could be delivered separately and assembled before use.

Advantageously, the tool 9" provides a stronger connection between the tool 9" and the disposable carrier 32 than may be made with a tool that connects with the lead extension connector 40. Such strong connection ensures that the disposable carrier 32 does not detach from the tool 9" while the disposable carrier 32 is being pulled through the tunnel. Additionally, the disposable carrier 32 provides protection for the lead extension connector 40 until the electrode lead extension 34 is in place and the lead extension connector 40 is removed from the disposable carrier 32.

A cross sectional view of the electrode lead extension 34 exiting the disposable carrier 32 through a lead guide 24 is illustrated in FIG. 8B. The view shown in FIG. 8B is taken along the section line 8B—8B of FIG. 8.

Turning next to FIG. 9, a second embodiment of a disposable carrier 32' is illustrated. The disposable carrier 32' includes a carrier break ring 38 that replaces the opening to the carrier cavity 28. Once the disposable carrier 32' has been carried through the tunnel, the disposable carrier 32' is broken at the carrier break ring 38 and discarded. When the disposable carrier 32' is broken at the carrier break ring 38, the disposable carrier separates into three parts along the carrier break joint 46 and the carrier break ring 38, thus allowing the lead extension connector 40 to be easily removed from the disposable carrier 32'. Advantageously, the disposable carrier 32' no longer requires an opening to the carrier cavity 28 that may snag on body tissue when it is carried through the tunnel. The disposable carrier 32' also provides secure containment for the lead extension connector 40 while the lead extension connector 40 is being carried through the cavity, and permits extraction of the lead extension connector 40 with negligible force. Various other methods of making a closed disposable carrier, which may be opened by breaking or flexing, will be apparent to those skilled in the art, and are intended to come within the scope of the present invention.

A cross sectional view of the disposable carrier 32' is shown in FIG. 9A taken along the section line 9A—9A of FIG. 9. Cooperation between a third mating connector 20" and a connector port 50 permits the disposable carrier 32' to pivot where it attaches to the mating connector 20" of the tool 9'". In FIG. 9A this is accomplished by lengthening the small diameter section of the mating connector 20", moving the garter spring 36 nearer to a rearward carrier end 42, and beveling the connector port 50 at a rearward carrier end 42 of the disposable carrier 32. Advantageously, when the disposable carrier 32 is pulled past bone or inflexible tissue, the ability to pivot reduces the force required to pull the carrier past such bone or tissue, and the disturbance of surrounding tissue is minimized. A variety of methods for creating a pivoting connection will be apparent to those skilled in the art and the device described here is an example of only one embodiment of many that are intended to come within the scope of the present invention.

A fourth embodiment of a tunneling and carrying tool, made in accordance with the present invention, comprises a tool 9'", as shown in FIG. 10. The tool 9'" comprises a second handle 10', a rod 12, a second carrier body 15', and a removable carrier cover 16'. In FIG. 10, the removable carrier cover 16' is in place over the carrier body 15'. The entire removable carrier cover 16' is in view, but just the rearward end of the carrier body 15' can be seen. The removable carrier cover 16' has a cover tunneling end 52 for tunneling.

The tool 9'" with the removable carrier cover 16' removed is shown in FIG. 10A. The lead extension connector 40 is shown inserted into the carrier body 15'.

Figure 11:
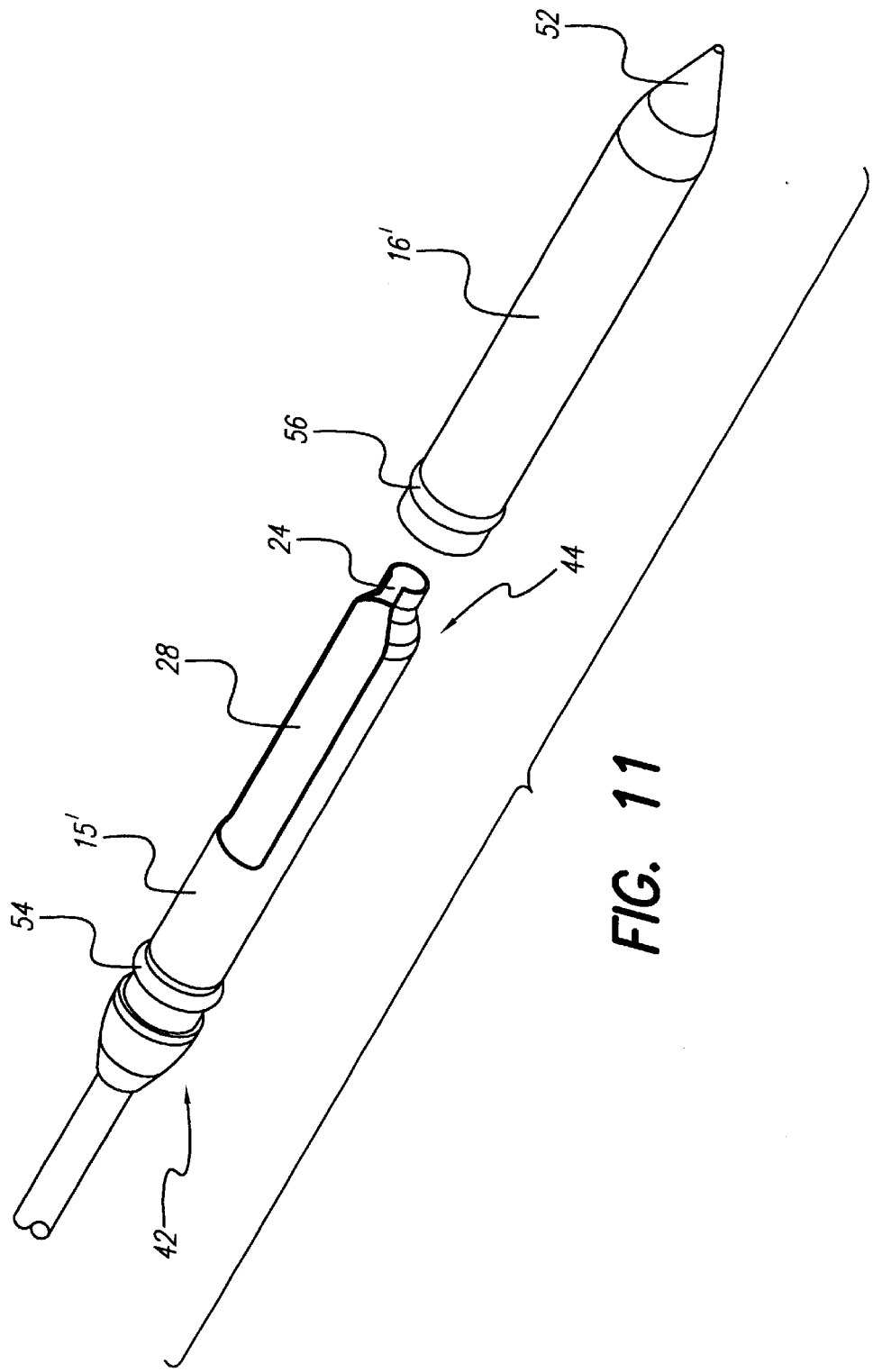
FIG. 11 shows a more detailed view of the carrier body and carrier cover of the fourth embodiment.

A detailed view of the carrier body 15' and removable carrier cover 16' are shown in FIG. 11. An O-ring 54 is held substantially captive in a groove in the exterior of the carrier body 15' near the rearward carrier end 42. The carrier cavity 28 is partially open to permit the insertion of the lead extension connector 40 therein. The lead guide 24 is provided at a forward carrier end 44. A section of the electrode lead extension 34 is inserted into the lead guide 24 to help secure the lead extension connector 40 in the carrier cavity 28. The removable carrier cover 16' includes an O-ring channel 56 on the end opposite the cover tunneling end 52. When the removable carrier cover 16' is slipped onto the carrier body 15', the O-ring 54 engages the O-ring channel 56 to retain the removable carrier cover 16' on the carrier body 15'. Those skilled in the art will recognize various other methods of retaining a carrier cover on a carrier body, and tunneling and carrying tools exercising those other methods are intended to come within the scope of the present invention.

While the invention herein disclosed has been described by means of specific embodiments and applications thereof, numerous modifications and variations could be made thereto by those skilled in the art without departing from the scope of the invention set forth in the claims.

What is claimed is:

1. A subcutaneous tunneling and carrying tool comprising;

a rod with a handle end and a carrier end;

a handle connected to said rod near said handle end;

means for both creating a tunnel and for carrying an electrode lead extension back through said tunnel, wherein said means for both creating a tunnel and for carrying is attached to said rod at said carrier end.

2. The tool of claim 1 wherein said means for both creating a tunnel and for carrying comprises a carrier wherein said carrier comprises a carrier forward end suitable for tunneling and a carrier cavity suitable for carrying a lead extension connector with attached electrode lead extension.

3. The tool of claim 1 wherein said means for both creating a tunnel and for carrying, comprises a carrier wherein;

said carrier comprises a carrier body and a carrier cover;

said carrier body includes a carrier cavity, wherein said electrode lead extension includes a lead extension connector, and wherein said lead extension connector is removably insertable into said carrier cavity; and said carrier cover includes a cover tunneling end.

4. The tool of claim 3 wherein the carrier cover is removably attachable to the carrier body, wherein when the carrier cover is attached, the carrier cavity is covered, and wherein when the carrier cover is removed, the carrier cavity is uncovered.

5. The tool of claim 4 wherein the carrier body includes a means for retaining the carrier cover, and the carrier cover includes a means for cooperating with the means for retaining.

6. The tool of claim 5 wherein the means for retaining comprises an O-ring held in a groove on the exterior of the carrier body, and wherein the means for cooperating comprises an O-ring channel in the carrier body, wherein the O-ring is substantially captive in the groove in the carrier body, and wherein the carrier cover is slid over the exterior of the carrier body and when the carrier cover is in place on the carrier body, the O-ring engages the O-ring channel.

7. The tool of claim 1 wherein the electrode lead extension is part of a Spinal Cord Stimulation (SCS) system.

8. A tool for forming a subcutaneous tunnel, and carrying an electrode lead extension of a Spinal Cord Stimulation (SCS) system back through the tunnel, the tool comprising;

a handle;

a rod with a handle end and a carrier end, wherein the handle is attached to the rod at the handle end;

a carrier, wherein the carrier is attached to the rod at the carrier end, and wherein the carrier includes means for tunneling and means for carrying.

9. The tool of claim 8 wherein the carrier has a forward carrier end pointed away from the rod, and a rearward carrier end pointed towards the rod, and wherein the means for tunneling comprises a shape of the forward carrier end to facilitate tunneling.

10. The tool of claim 8 wherein the carrier includes a carrier cavity, and wherein the means for carrying comprises the carrier cavity.

11. The tool of claim 10 wherein the electrode lead extension includes a lead extension connector, and wherein the lead extension connector is removably insertable into the carrier cavity.

12. The tool of claim 10 wherein the carrier further includes:
- a forward carrier end pointed away from the rod;
- a rearward carrier end pointed towards the rod;
- a carrier body; and
- a removable carrier cover;
- wherein the carrier cavity is in the carrier body, and wherein the removable carrier cover is removably instalable onto the carrier body by sliding the carrier cover over the forward carrier end of the carrier body, and wherein the means for tunneling comprises a substantially pointed end on the carrier cover pointed away from the rod.

13. The tool of claim 12 wherein the carrier body includes a means for retaining the carrier cover, and the carrier cover includes a means for cooperating with the means for retaining.

14. The tool of claim 13 wherein the means for retaining comprises an O-ring held in a groove on the exterior of the carrier body, and wherein the means for cooperating comprises an O-ring channel in the carrier body, wherein the O-ring is substantially captive in the groove in the carrier body, and wherein the carrier cover is slid over the exterior of the carrier body and when the carrier cover is in place on the carrier body, the O-ring engages the O-ring channel.

15. A method for making a subcutaneous tunnel and carrying an electrode lead extension through the tunnel, comprising:

- inserting a tunneling and carrying tool through an incision, which tool comprises means for both creating a tunnel and for carrying an electrode lead extension back through said tunnel;
- creating a subcutaneous tunnel by pushing the tool through tissue;
- inserting the electrode lead extension into the tool; and
- carrying the electrode lead extension to the site of the incision.

16. The method of claim 15 wherein the electrode lead extension includes a lead extension connector, and wherein inserting the electrode lead extension comprises inserting the lead extension connector into the tool.

17. The method of claim 15 wherein the electrode lead extension includes a lead extension connector, and wherein the tool includes a carrier body and a removable carrier cover, and wherein inserting the electrode lead extension comprises:

- removing the carrier cover; and
- inserting the lead extension connector into the carrier body.

18. The method of claim 15 wherein the electrode lead extension is part of a Spinal Cord Stimulation (SCS) system.

* * * * *

UNITED STATES PATENT AND TRADEMARK OFFICE
CERTIFICATE OF CORRECTION

PATENT NO.      : 6,605,094 B1                                         Page 1 of 1
DATED           : August 12, 2003
INVENTOR(S)     : Mann et al.

It is certified that error appears in the above-identified patent and that said Letters Patent is hereby corrected as shown below:

<u>Title page,</u>
Item [74], *Attorney, Agent or Firm*, add -- Kenneth L. Green --.

Signed and Sealed this

Second Day of December, 2003

JAMES E. ROGAN
*Director of the United States Patent and Trademark Office*